US00RE48119E

(19) United States
(12) Reissued Patent
de Beaubien

(10) Patent Number: US RE48,119 E
(45) Date of Reissued Patent: *Jul. 28, 2020

(54) ANTIBIOTIC DELIVERY SYSTEM AND METHOD FOR TREATING AN INFECTED SYNOVIAL JOINT DURING RE-IMPLANTATION OF AN ORTHOPEDIC PROSTHESIS

(71) Applicant: Joint Purification Systems, Inc., Solana Beach, CA (US)

(72) Inventor: Brian C. de Beaubien, Fenton, MI (US)

(73) Assignee: Joint Purification Systems, Inc., Solana Beach, CA (US)

( * ) Notice: This patent is subject to a terminal disclaimer.

(21) Appl. No.: 15/846,021

(22) Filed: Dec. 18, 2017

Related U.S. Patent Documents

Reissue of:
(64) Patent No.: 8,900,322
Issued: Dec. 2, 2014
Appl. No.: 13/759,239
Filed: Feb. 5, 2013

U.S. Applications:
(60) Continuation of application No. 15/336,472, filed on Oct. 27, 2016, now Pat. No. Re. 46,669, which is a
(Continued)

(51) Int. Cl.
*A61F 2/30* (2006.01)
*A61F 2/38* (2006.01)
(Continued)

(52) U.S. Cl.
CPC ..... *A61M 37/00* (2013.01); *A61F 2/36* (2013.01); *A61F 2/38* (2013.01)

(58) Field of Classification Search
CPC ..... A61F 2/367; A61F 2220/0033
(Continued)

(56) References Cited

U.S. PATENT DOCUMENTS 4,274,163 A * 6/1981 Malcom et al. ..... 606/94
4,399,814 A * 8/1983 Pratt et al. ..... 606/94
(Continued)

FOREIGN PATENT DOCUMENTS

EP 2943164 B1 3/2017
WO WO-2016205077 A1 12/2016

OTHER PUBLICATIONS

International Search Report and Written Opinion dated Sep. 8, 2016 for International PCT Patent Application No. PCT/US2016/036761.
(Continued)

*Primary Examiner* — Beverly M Flanagan
(74) *Attorney, Agent, or Firm* — Wilson Sonsini Goodrich & Rosati

(57) ABSTRACT

An antibiotic delivery system including an intramedullary stem that is adapted to be removably mounted into a medullary canal of a bone. The stem includes a body having an inlet adapted to be in fluid communication with a source of liquid-borne antibiotic and a plurality of outlets disposed along the stem. A channel extends between the inlet and the plurality of outlets for delivering a fluid-borne antibiotic from the inlet to the plurality of outlets so as to distribute the antibiotic along the medullary canal in a controlled fashion. A method of treating an infected joint during a two-stage re-implantation of an orthopedic implant is also disclosed.

30 Claims, 9 Drawing Sheets

Related U.S. Application Data continuation of application No. 14/817,103, filed on Aug. 3, 2015, now Pat. No. Re. 46,283, which is an application for the reissue of Pat. No. 8,900,322, which is a division of application No. 12/712,748, filed on Feb. 25, 2010, now Pat. No. 8,454,706.

(60) Provisional application No. 61/208,540, filed on Feb. 25, 2009.

(51) Int. Cl.

| | |
|---|---|
| ***A61M 37/00*** | (2006.01) |
| ***A61F 2/36*** | (2006.01) |
| ***A61F 2/48*** | (2006.01) |
| ***A61F 2/46*** | (2006.01) |

(58) Field of Classification Search

USPC ..... 623/16.11, 18.11, 19.12, 20.14, 20.21, 623/22.11, 23.15, 23.29

See application file for complete search history.

(56) References Cited

U.S. PATENT DOCUMENTS

| | | | | |
|---|---|---|---|---|
| 4,488,549 | A * | 12/1984 | Lee et al. | 606/94 |
| 4,653,487 | A | 3/1987 | Maale | |
| 4,711,233 | A * | 12/1987 | Brown | 606/81 |
| 4,888,024 | A * | 12/1989 | Powlan | 623/23.19 |
| 4,892,550 | A * | 1/1990 | Huebsch | 623/23.19 |
| 5,116,377 | A * | 5/1992 | Skripitz et al. | 623/23.19 |
| 5,133,767 | A * | 7/1992 | Frey et al. | 623/23.54 |
| 5,133,771 | A * | 7/1992 | Duncan et al. | 623/23.2 |
| 5,133,772 | A * | 7/1992 | Hack et al. | 623/23.19 |
| 5,156,606 | A | 10/1992 | Chin | |
| 5,290,291 | A | 3/1994 | Linden | |
| 5,340,362 | A * | 8/1994 | Carbone | 623/23.19 |
| 5,370,698 | A | 12/1994 | Heimke et al. | |
| 5,376,123 | A * | 12/1994 | Klaue et al. | 623/23.19 |
| 5,433,718 | A * | 7/1995 | Brinker | 606/62 |
| 5,501,687 | A * | 3/1996 | Willert et al. | 606/94 |
| 5,514,137 | A * | 5/1996 | Coutts | 606/62 |
| 5,554,111 | A * | 9/1996 | Morrey et al. | 606/26 |
| 5,562,736 | A * | 10/1996 | Ray et al. | 606/86 A |
| 5,571,204 | A | 11/1996 | Nies | |
| 5,618,286 | A | 4/1997 | Brinker | |
| 5,681,289 | A | 10/1997 | Wilcox et al. | |
| 5,683,472 | A | 11/1997 | O'Neil et al. | |
| 5,702,446 | A | 12/1997 | Schenck et al. | |
| 5,725,596 | A | 3/1998 | Burke | |
| 5,741,265 | A | 4/1998 | Chan | |
| 5,755,811 | A | 5/1998 | Tanamal et al. | |
| 5,827,289 | A | 10/1998 | Reiley et al. | |
| 5,954,771 | A | 9/1999 | Richelsoph et al. | |
| 5,980,573 | A * | 11/1999 | Shaffner | 128/898 |
| 6,066,154 | A | 5/2000 | Reiley et al. | |
| 6,113,639 | A * | 9/2000 | Ray et al. | 623/17.16 |
| 6,155,812 | A * | 12/2000 | Smith et al. | 425/318 |
| 6,217,619 | B1 | 4/2001 | Keller | |
| 6,235,043 | B1 | 5/2001 | Reiley et al. | |
| 6,248,110 | B1 | 6/2001 | Reiley et al. | |
| 6,361,731 | B1 * | 3/2002 | Smith et al. | 264/271.1 |
| 6,361,780 | B1 * | 3/2002 | Ley et al. | 424/400 |
| 6,423,083 | B2 | 7/2002 | Reiley et al. | |
| 6,447,514 | B1 | 9/2002 | Stalcup et al. | |
| 6,544,472 | B1 * | 4/2003 | Compton et al. | 419/2 |
| 6,589,281 | B2 | 7/2003 | Hyde, Jr. | |
| 6,679,890 | B2 | 1/2004 | Margulies et al. | |
| 6,740,090 | B1 * | 5/2004 | Cragg et al. | 606/79 |
| 6,740,120 | B1 * | 5/2004 | Grimes | 623/22.12 |
| 6,783,515 | B1 | 8/2004 | Miller et al. | |
| 6,921,403 | B2 * | 7/2005 | Cragg et al. | 606/86 R |
| 6,942,702 | B2 | 9/2005 | Mitsugi et al. | |
| 6,969,404 | B2 * | 11/2005 | Ferree | 623/17.11 |
| 6,979,336 | B2 * | 12/2005 | Durniak | 606/92 |
| 6,981,981 | B2 | 1/2006 | Reiley et al. | |
| 6,989,033 | B1 * | 1/2006 | Schmidt | 623/23.51 |
| 7,048,743 | B2 | 5/2006 | Miller et al. | |
| 7,112,205 | B2 | 9/2006 | Carrison | |
| 7,141,053 | B2 | 11/2006 | Rosa et al. | |
| 7,211,113 | B2 | 5/2007 | Zelener et al. | |
| 7,250,055 | B1 * | 7/2007 | Vanderwalle | 606/92 |
| 7,255,713 | B2 * | 8/2007 | Malek | 623/17.12 |
| 7,306,629 | B2 | 12/2007 | Saladino et al. | |
| 7,427,296 | B2 * | 9/2008 | Evans | 623/20.14 |
| 7,429,346 | B2 * | 9/2008 | Ensign et al. | 264/264 |
| 7,534,240 | B1 | 5/2009 | Johnson | |
| 7,572,293 | B2 * | 8/2009 | Rhodes et al. | 623/20.32 |
| 7,601,157 | B2 | 10/2009 | Boyd et al. | |
| 7,601,176 | B2 | 10/2009 | Soffiati et al. | |
| 7,862,619 | B2 | 1/2011 | Clark | |
| 7,914,585 | B2 * | 3/2011 | Keller | 623/23.26 |
| 8,038,682 | B2 | 10/2011 | McGill et al. | |
| 8,097,039 | B2 * | 1/2012 | Evans | 623/20.14 |
| 8,135,466 | B2 * | 3/2012 | Fuller et al. | 607/22 |
| 8,388,881 | B2 * | 3/2013 | Giori | 264/250 |
| 8,454,706 | B2 * | 6/2013 | de Beaubien | 623/23.39 |
| 8,652,216 | B2 * | 2/2014 | Chen et al. | 623/23.72 |
| 8,673,018 | B2 * | 3/2014 | Walls | 623/23.57 |
| 8,685,432 | B2 * | 4/2014 | Evans et al. | 424/426 |
| 8,721,520 | B2 * | 5/2014 | Caira et al. | 600/30 |
| 8,900,322 | B2 | 12/2014 | De | |
| 8,900,323 | B2 | 12/2014 | De | |
| RE46,283 | E | 1/2017 | De Beaubien | |
| RE46,669 | E | 1/2018 | De Beaubien | |
| 2001/0051831 | A1 | 12/2001 | Subba et al. | |
| 2003/0060891 | A1 * | 3/2003 | Shah | 623/22.13 |
| 2003/0097184 | A1 | 5/2003 | Mitsugi et al. | |
| 2003/0187513 | A1 * | 10/2003 | Durniak | 623/22.12 |
| 2004/0036189 | A1 * | 2/2004 | Ensign et al. | 264/40.1 |
| 2004/0193281 | A1 * | 9/2004 | Grimes | 623/22.12 |
| 2004/0225360 | A1 * | 11/2004 | Malone | 623/17.11 |
| 2005/0021084 | A1 * | 1/2005 | Lu et al. | 606/218 |
| 2005/0187555 | A1 * | 8/2005 | Biedermann et al. | 606/72 |
| 2005/0277936 | A1 | 12/2005 | Siravo et al. | |
| 2006/0014120 | A1 * | 1/2006 | Sapian | 433/173 |
| 2006/0030945 | A1 | 2/2006 | Wright et al. | |
| 2006/0093646 | A1 * | 5/2006 | Cima et al. | 424/425 |
| 2006/0121083 | A1 * | 6/2006 | Mor | 424/426 |
| 2007/0005142 | A1 | 1/2007 | Rhodes et al. | |
| 2007/0110804 | A1 * | 5/2007 | Royer | 424/468 |
| 2007/0123835 | A1 | 5/2007 | Molander et al. | |
| 2009/0069899 | A1 * | 3/2009 | Klein | 623/22.4 |
| 2009/0130167 | A1 | 5/2009 | Shelton et al. | |
| 2010/0042167 | A1 * | 2/2010 | Nebosky et al. | 606/315 |
| 2010/0042213 | A1 * | 2/2010 | Nebosky et al. | 623/16.11 |
| 2010/0042214 | A1 * | 2/2010 | Nebosky et al. | 623/16.11 |
| 2010/0042215 | A1 * | 2/2010 | Stalcup et al. | 623/16.11 |
| 2010/0114324 | A1 | 5/2010 | Gibbs et al. | |
| 2010/0217401 | A1 * | 8/2010 | de Beaubien | 623/20.34 |
| 2010/0292803 | A1 * | 11/2010 | Giori | 623/20.14 |
| 2011/0208315 | A1 | 8/2011 | Anapliotis et al. | |
| 2011/0236501 | A1 * | 9/2011 | Guelcher et al. | 424/549 |
| 2013/0041472 | A1 * | 2/2013 | Rabiner et al. | 623/18.11 |
| 2013/0209522 | A1 * | 8/2013 | Brooks et al. | 424/400 |
| 2013/0211334 | A1 * | 8/2013 | de Beaubien | 604/175 |
| 2013/0211369 | A1 * | 8/2013 | de Beaubien | 604/500 |
| 2013/0289621 | A1 | 10/2013 | Fulmer et al. | |
| 2014/0194811 | A1 | 7/2014 | Barsoum et al. | |
| 2014/0277532 | A1 | 9/2014 | Teeny et al. | |
| 2015/0038941 | A1 | 2/2015 | Nebosky et al. | |
| 2016/0367371 | A1 | 12/2016 | De et al. | |

OTHER PUBLICATIONS

Notice of allowance dated Feb. 22, 2013 for U.S. Appl. No. 12/712,748.

Notice of Allowance dated Jul. 29, 2016 for U.S. Appl. No. 14/817,103.

Notice of Allowance dated Aug. 24, 2017 for U.S. Appl. No. 15/336,472.

Notice of allowance dated Aug. 27, 2014 for U.S. Appl. No. 13/759,239.

(56) References Cited

OTHER PUBLICATIONS

Notice of allowance dated Aug. 27, 2014 for U.S. Appl. No. 13/759,253.
Notice of allowance dated Sep. 6, 2016 for U.S. Appl. No. 14/817,103.
Office action dated Feb. 19, 2016 for U.S. Appl. No. 14/817,103.
Office action dated Feb. 22, 2012 for U.S. Appl. No. 12/712,748.
Office action dated Mar. 21, 2014 for U.S. Appl. No. 13/759,253.
Office action dated Mar. 24, 2014 for U.S. Appl. No. 13/759,239.
Office Action dated Mar. 31, 2017 for U.S. Appl. No. 15/336,472.
Office action dated Sep. 10, 2012 for U.S. Appl. No. 12/712,748.
Notice of Allowance dated Oct. 6, 2017 for U.S. Appl. No. 15/336,472.
U.S. Appl. No. 14/841,529 Office Action dated Apr. 10, 2018.
U.S. Appl. No. 14/841,529 Office Action dated Feb. 7, 2019.

* cited by examiner

ANTIBIOTIC DELIVERY SYSTEM AND METHOD FOR TREATING AN INFECTED SYNOVIAL JOINT DURING RE-IMPLANTATION OF AN ORTHOPEDIC PROSTHESIS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

*Notice: More than one reissue application has been filed for the reissue of U.S. Pat. No. 8,900,322. The reissue applications are U.S. patent application Ser. Nos. 15/846,021, 15/336,472, and 14/817,103. More particularly, U.S. patent application Ser. No. 15/846,021 (the present application) is a continuation reissue application of U.S. patent application Ser. No. 15/336,472, filed Oct. 27, 2016, now U.S. Reissue Pat. No. RE46,669, issued Jan. 16, 2018, which is a continuation reissue application of U.S. patent application Ser. No. 14/817,103, filed on Aug. 3, 2015, now U.S. Reissue Pat. No. RE46,283, issued Jan. 24, 2017, which sought reissue of U.S. patent application Ser. No. 13/759,239, filed Feb. 5, 2013, now U.S. Pat. No. 8,900,322, issued Dec. 2, 2014.*

CROSS-REFERENCE TO RELATED APPLICATION(S)

[This application] *U.S. patent application Ser. No. 13/759,239, filed Feb. 5, 2013, now U.S. Pat. No. 8,900,322, issued Dec. 2, 2014,* is a divisional of U.S. patent application *Ser. No. 12/712,748, filed Feb. 15, 2010, now U.S. Pat. No. 8,545,706, issued Jun. 4, 2013, and* entitled "Antibiotic Delivery System and Method for Treating an Infected Synovial Joint During Re-implantation of an Orthopedic Prosthesis," [having U.S. Ser. No. 12/712,748, and filed Feb. 25, 2010,] which claims the benefit of U.S. [provisional patent application] *Provisional Patent Application Ser. No. 61/208,540, filed Feb. 25, 2009, now expired, and* entitled "Joint Purification Systems[.]." [having Ser. No. 61/208,540, and filed on Feb. 25, 2009.]

BACKGROUND OF THE INVENTION

1. Field of the Invention

The present invention relates, generally, to an antibiotic delivery system and, more specifically, to such a system and method for treating an infected synovial joint and adjacent medullary canals as a means of eliminating infection during a two-stage re-implantation of an orthopedic prosthesis.

2. Description of the Related Art

A total joint replacement (TJR) is a medical procedure that involves the repair and replacement of joints, such as hips and knees. In these cases, the bones at the hip or knee joints are prepared in receive orthopedic implants that mimic the structure of the joint that is replaced. For example, a total knee replacement is representatively shown at 10 in FIG. 1. The total knee replacement 10 includes tibial 12 and femoral 14 components that imitate the structure and function of the natural knee joint. The tibial component 12 is operatively mounted to the tibia bone 16 and the femoral component 14 is operatively mounted to the femoral bone (not shown).

Similarly, a total hip replacement includes a femoral component that terminates in a neck having a hemispherical ball that mimics the upper terminal portion of the natural femoral bone.

Currently, there are approximately one million total joint replacement (TJR) surgeries involving either hips or knees performed annually in the United States. Obviously, more TJR surgeries are performed throughout the world. However, the demand for TJR surgery is expected to soar in the future. Doctor-diagnosed arthritis is expected to increase 40% from 2005 to 2030. According to the 2003 National Institute of Health Census Panel Report on total knee replacement, only 9% to 13% of TJR candidates have been willing to undergo the procedure. As patients become more aware of their options, as well as the success of TJR, demand may reach even higher levels.

Baby boomers will start reaching the age of 65 years in 2011. Also, over the past decade, the prevalence of TJR has increased not only in older patients (those who are 65 years or older) but also in younger patients (those less than 65 years old). Premium implant technology such as hard-on-hard bearings and hip resurfacing have been introduced to address the increased activity and longevity of younger patients. The demand for primary total hip and total knee replacements on patients younger than 65 years old was projected to exceed 50% of joint replacement recipients by 2011 and 2013, respectively. Demand for primary total hip replacement is expected to grow 174% and for total knee replacement by 673% by the year 2030. Data collected from the U.S. Nationwide Implant Sample (NIS) between 1993 and 2005 has also been evaluated. This data indicates that by 2030 future demand of primary and revision TJR procedures (where an older implant is replaced with a new one) will be significant. For example, primary total knee replacements are projected to be 4,580,000. The need to revise and re-implant total knee replacements is projected to be 269,000. Primary total hip replacements are projected to be 975,000. And the need to revise and re-implant total hip replacements is projected to be 103,000 per year. These estimated projections total 6,000,000 TJR surgeries annually.

In relatively rare cases, however, infection is a devastating complication of TJR surgeries. The rate of infection in these types of surgeries ranges between 0.5% and 1.5%. Unless an infection is properly diagnosed within the first two to four weeks following the original surgery (which is uncommon), the infected implant must be removed in combination with an extensive debridement of the surrounding joint tissue and bone. According to the Center for Disease Control, there are currently approximately 12,000 infected TJR cases annually in the United States. Obviously, this number increases when the entire worldwide scope of TJR surgeries is considered. At 1% infection rate, and assuming the projections noted above are generally accurate, there will be 60,000 instances of infected total joints annually in the future.

Over the past two decades, the standard of care for treatment of an infected TJR in the United States has included a two-stage re-implantation process. In the first stage of this process, the infected components are surgically exposed by incision. Scar tissue is then de-bulked as well as other soft tissue releases, and sometimes an osteotomy. This stage also includes the removal of all prosthetic components and foreign material including, for example, acrylic bone cement. After extensive joint debridement of infected soft tissue and bone, a spacer block consisting of heavily dosed antibiotic bone cement is placed temporarily into the joint space. The purpose of the antibiotic bone cement is to sterilize the joint environment and to serve as an antibiotic delivery system. Additionally, the bone cement acts as a spacer to preserve joint space and maintains ligament length. However, the antibiotic released by the bone cement is uncontrolled and is quite costly to use. For example, a typical knee spacer may require three bags of acrylic bone cement, twelve vials of an antibiotic such as Tobramycin (1.2 g) at a cost of $800 per vial, and six vials of an antibiotic such as Vancomycin (1 g) at $17 per vial. This quickly adds up to about $11,000 in material alone. In addition, more operating room time is necessary to prepare this spacer material. This increases the cost of the operation.

Under the current standard of care, following the removal of the infected implant and the insertion of the antibiotic bone cement spacer, the patient must generally wait between six and, more typically, twelve weeks before the second stage of the procedure can be performed. This period of time is necessary so that the medical professionals can be confident that the infection has been successfully eradicated. Only after the infectious condition has been eliminated, may the second stage proceed. During the second stage, the new prosthesis is re-implanted. The success rate with this two-stage re-implantation process is typically around 90%.

In other countries, such as throughout Europe, a one-stage re-implantation process has been popular. This involves the removal of the infected implant, as noted above, followed by aggressive debridement and then immediate re-implantation of a new implant. The success rate for this technique has typically been in the 70%-85% range. However, this technique has not gained popularity to any degree in the United States. The one-state implantation process is generally reserved for patients who are considered to be too feeble or sick to undergo the traditional two-stage re-implantation process.

Both the one-stage and two-stage surgical re-implantation protocols have their disadvantages. For example, and as noted above, the two-stage re-implantation process requires six to twelve weeks between operations. This is a very difficult time for the patient as they do not have a functional joint in place and it is typically very painful to mobilize or ambulate with an antibiotic spacer. Articulating spacers are somewhat better than static spacers, but are also more expensive as well as more difficult and time-consuming to place during the original stage one procedure. From a health care standpoint, the two-stage procedure also requires two separate hospitalizations. Finally, from a surgeon's standpoint, a significant amount of scar tissue develops during the time span between the two procedures. This makes for a very difficult and time-consuming second stage operation. In addition, the two-stage re-implantation process involves not one, but two, very difficult surgical procedures. The estimated cost of removing the infected original implant, eliminating the infection, extended hospitalization, nursing home care or home health care during the period between the first and second operations, a well as re-implanting a new prosthesis is currently roughly $100,000 per case. This is a tremendous overall burden on the universal health care system and, in the United States alone, reaches approximately $1.2 billion per year. This statistic does not begin to measure losses in patient economic productivity, quality of life, as well as pain and suffering. Moreover, this statistic does not reflect the costs associated with the projected increase in TJR operations in the future as noted above.

On the other hand, a one-stage re-implantation surgical protocol requires absolute identification of the infecting organism in order to proceed. Unfortunately, it is very difficult to achieve this absolute identification in the current health care systems. In addition, a one-stage re-implantation protocol requires the use of fully-cemented components. Fully-cemented components are typically not favored by U.S. surgeons for revision surgery. Fully-cemented components typically require very high amount of antibiotic. This often is as high as 10% by weight. For example, 4 g of antibiotic are required for a 40 g bag of cement. The increase of antibiotic by weight raises concerns regarding structural weakening of the cement.

Moreover, and in both one-stage and two-stage re-implantation surgical protocols, the release of the antibiotic from the bone cement is completely uncontrolled. This is a significant disadvantage of both protocols and essentially acts to lengthen the time between the first and the second surgical procedures in the two-stage re-implantation process.

Thus, there remains a need in the art for a device that may be employed during re-implantation surgical procedures that may be used to deliver antibiotic in a controlled and titratable manner directly into the synovial joint cavity and adjoining medullary canals as a means of eliminating the infection following the removal of a previous orthopedic implant. In addition, there remains a need in the art for such a device that can provide stability and maintain the physical dimensions of joint space and normal soft tissue envelope in any joint under-going the re-implantation of an orthopedic implant. In addition, there remains a need in the art for such a device that may be easily employed, facilitates the reduction in the time needed to conduct the stage one re-implantation surgery and that reduces the overall time between the first and second stages of a two-stage re-implantation surgical protocol.

SUMMARY OF THE INVENTION

The present invention is directed toward an antibiotic delivery system including a device and method for treating an synovial joint and adjacent tissues, including bone, during the re-implantation of an orthopedic prosthesis. The antibiotic delivery device includes an intramedullary stem adapted to be removably mounted in a medullary canal of a bone. The stem includes an inlet adapted to be in fluid communication with a source of fluid-borne antibiotic, a plurality of outlets disposed along the stem and a channel extending between the inlet and the plurality of outlets for delivering fluid-borne antibiotic from the inlet to the plurality of outlets so as to distribute the antibiotic along the medullary canal in a controlled fashion.

In addition, the present invention is also directed toward a method of treating an infected synovial joint and adjacent tissue during a two-stage re-implantation of an orthopedic implant. The method includes the steps of removing the infected implant mounted to the medullary canal of a bone and debriding the medullary canal. An intramedullary stem is then installed into the medullary canal. The stem includes an inlet, a plurality of outlets, and a channel extending between the inlet and the plurality of outlets. In addition, the method includes the step of providing a source of fluid-borne antibiotic to the inlet of the intramedullary stem so as to distribute the antibiotic through the channel and outlets into the medullary canal in a controlled fashion.

The antibiotic delivery system of the present invention, as well as the method overcomes the disadvantages in the related art in providing a modular, implantable device designed for short-term use of approximately one week as a part of an abbreviated two-stage re-implantation technique for treatment of septic TJR of either the knee or the hip. The present invention provides structural rigidity to the joint and the limb during the period of time between the removal of an infected prosthesis and the re-insertion of a new prosthesis. This allows the patient to be mobile, while minimizing pain. The present invention also eliminates the need for an external stabilizing device, such as a cast, between the first and second stages of the re-implantation process. In addition, the system maintains joint space while acting as a temporary spacer. As explained in greater detail below, the implant assembly maintains the proper length of vital structures, including ligaments, muscles, tendons, neurovascular structures, etc., until the new prosthesis can be implanted. The system and method of the present invention act to deliver a controlled titratable antibiotic dosed directly into the synovial joint cavity and the medullary canals via an infusion system thereby attaining and maintaining much higher local joint space and tissue levels of antibiotics than can be obtained by current antibiotic spacers (static or articulating) as well as perental/I.V.-administered antibiotics. In addition, the system and method of the present invention act to irrigate and cleanse the synovial joint and medullary canals through a novel concept utilizing intermittent pulsatile levage. In this way, the present invention facilitates the reduction in the time between the first and second stages of a two-stage re-implantation process from six to twelve weeks under the current standard of care to approximately one week.

Other objects, features, and advantages of the present invention will be readily appreciated as the same becomes better understood while reading the subsequent description taken in conjunction with the accompanying drawings.

BRIEF DESCRIPTION OF THE. DRAWINGS

DETAILED DESCRIPTION OF THE INVENTION

Figure 1:
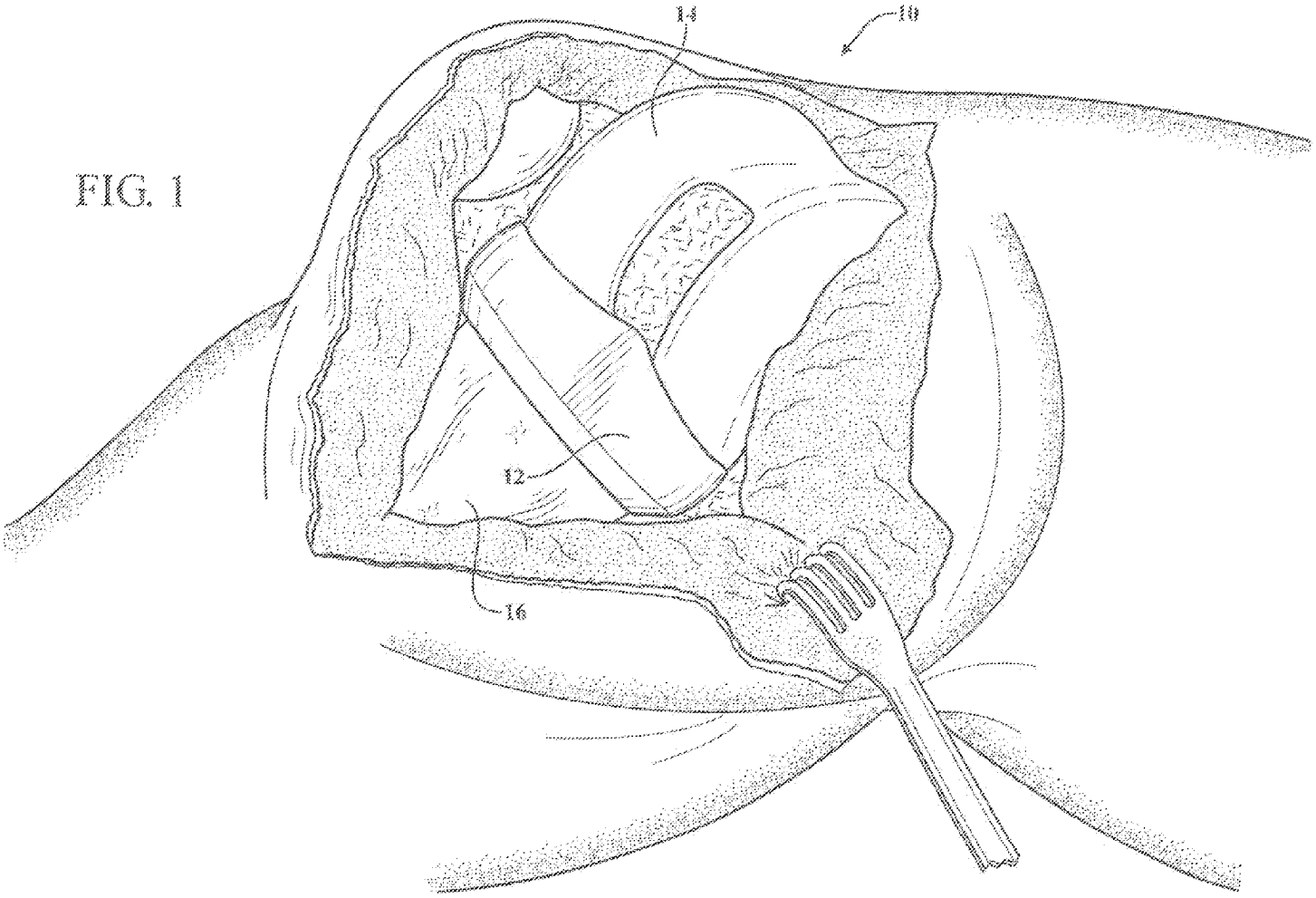
FIG. 1 is a perspective view illustrating a surgically exposed total joint replacement of a knee.
Figure 2:
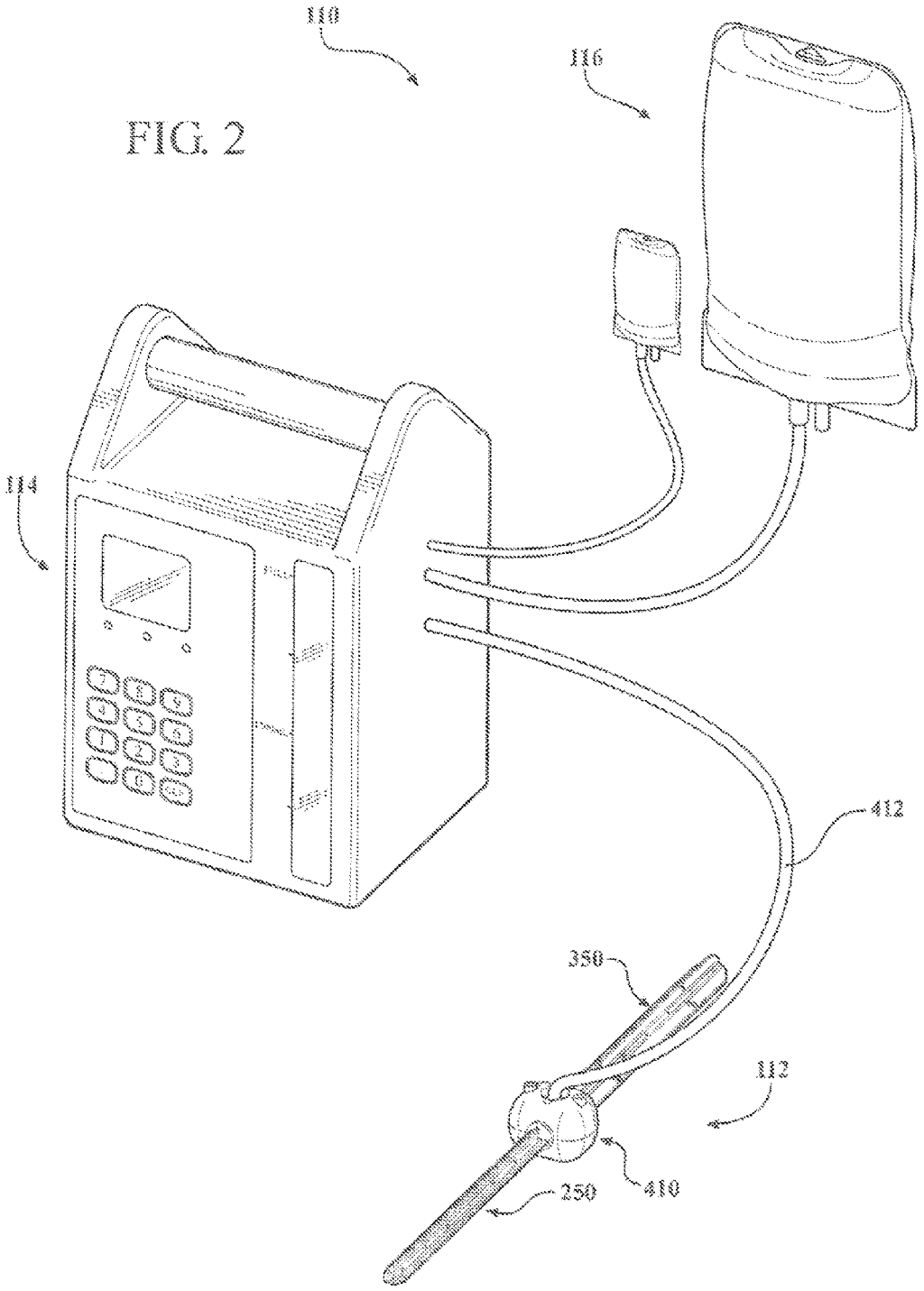
FIG. 2 is a perspective view of the antibiotic delivery system of the present invention.

One embodiment of an antibiotic delivery system according to the present invention is generally indicated at 110 in FIG. 2, where like numerals are used to designate like structure throughout the figures. The antibiotic delivery system 110 includes an implant assembly, generally indicated at 112, a pump, generally indicated at 114, and a source of fluid-borne antibiotic, generally indicated at 116. The antibiotic implant assembly 112 forms one component of the antibiotic delivery system 110. One of the assembly's basic components includes an intramedullary stem. One embodiment of the intramedullary stem is generally indicated at 118 in FIGS. 3-5. In the case of a total knee replacements the assembly 112 includes a tibial intramedullary stem, generally indicated at 250, and a femoral intramedullary stem, generally indicated at 350 in FIGS. 7-12. Each of these components will be described in greater detail below.

More specifically, various features of the intramedullary stem will now be described with respect to the embodiment designated 118 in FIGS. 3-5. Those having ordinary skill in the art will appreciate that the features described with respect to the embodiment illustrated in these figures are also generally present in the other embodiments described below. The intramedullary stem 118 is adapted to be removably mounted into a medullary canal of a bone. The stem 118 includes an inlet 120 that is adapted to be in fluid communication with the source of fluid-borne antibiotic 116 and other appropriate fluids, as will be described in greater detail below. In addition, the stem 118 includes a plurality of outlets 122 that are disposed along the stem 118. In addition, a channel 124 (FIG. 4A) extends between the inlet 120 and the plurality of outlets 122 for delivering fluid-borne antibiotic from the inlet 120 to the plurality of outlets 122 so as to distribute the antibiotic along the medullary canal in a controlled fashion.

Figure 3:
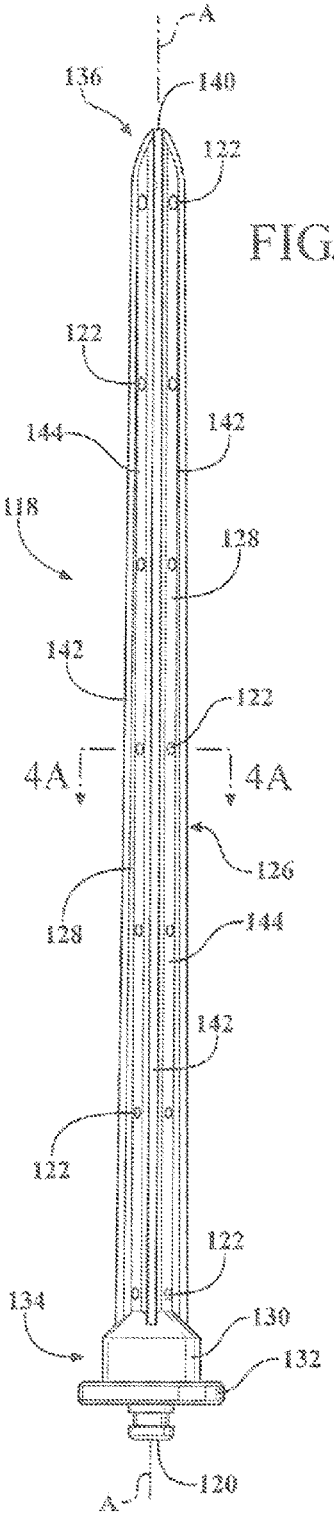
FIG. 3 is an elevational view of one embodiment of an intramedullary stem of the present invention.
Figure 4:
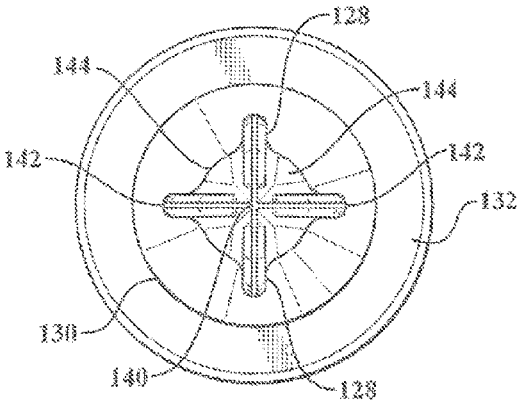
FIG. 4 is an end view of the distal end of the intramedullary stem illustrated in FIG. 3.
Figure 4A:
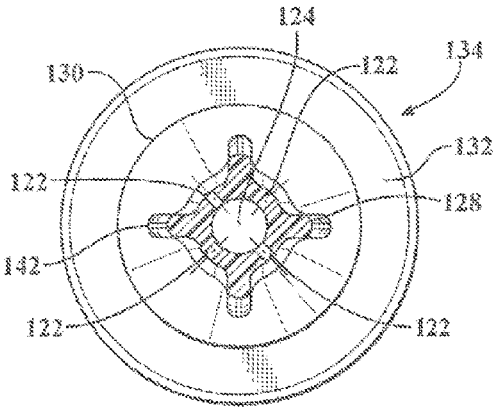
FIG. 4A is a cross-sectional view taken along lines 4A-4A of FIG. 3.
Figure 5:
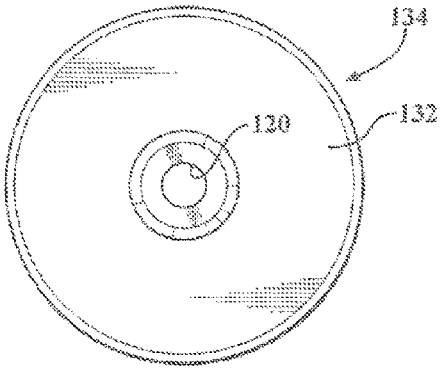
FIG. 5 is an end view of the proximal end of the intramedullary stem illustrated in FIG. 3.
Figure 12:
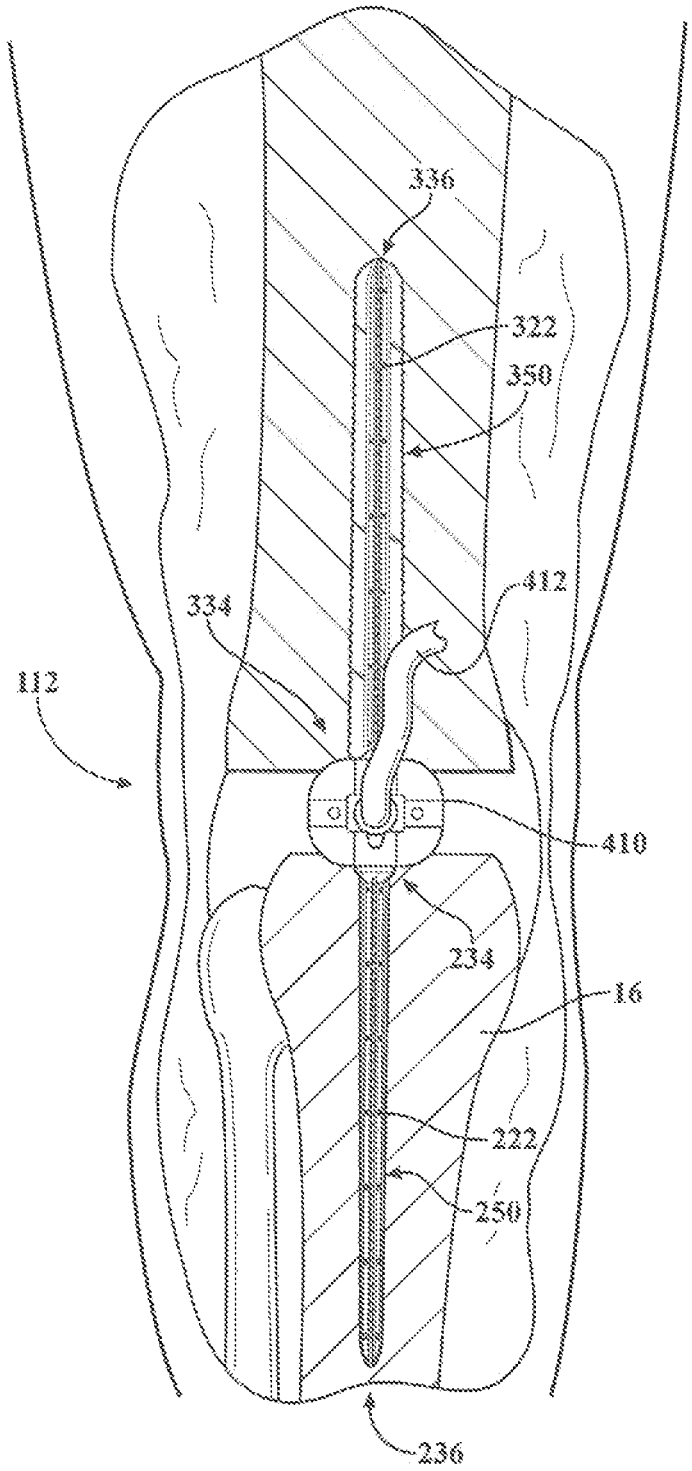
FIG. 12 is a partial cross-sectional plan view illustrating the implant assembly mounted in a human knee joint.
Figure 13:
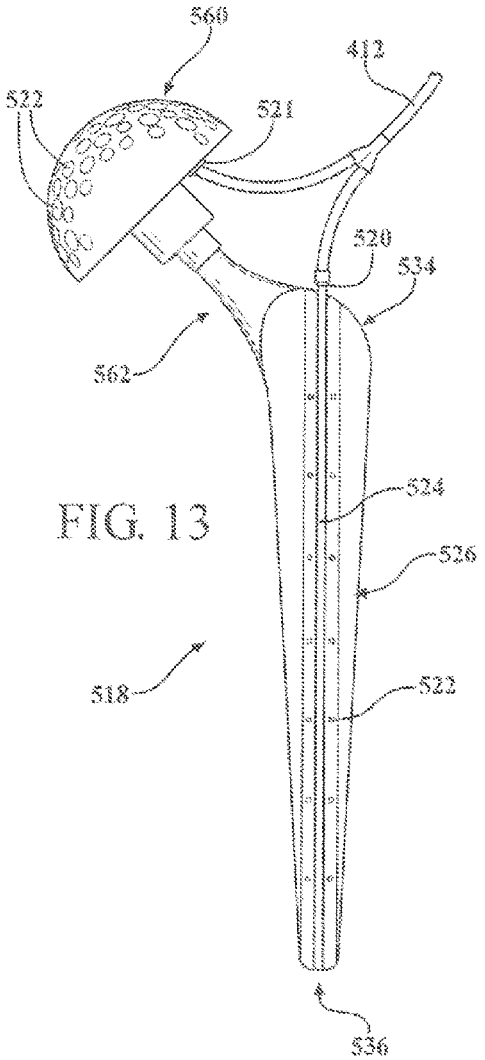
FIG. 13 is a partial cross-sectional side view of an alternate embodiment of the femoral intramedullary stem of the present invention.

In the embodiment illustrated in FIGS. 3-5, the antibiotic implant assembly 112 and the intramedullary stem 118, per se, is particularly adapted for use in connection with the first stage of a re-implantation of a total knee replacement where the first implant has become infected. As explained in greater detail below and as illustrated in FIG. 12, the antibiotic implant assembly 112 of the present invention may also be particularly adapted for use in the first stage of a total hip replacement where the first implant has become infected. Each of these assemblies will be described in greater detail below.

Referring now specifically to the device as it is employed in connection with a re-implantation of a knee, the intramedullary stem 118 illustrated in FIGS. 3-5 defines a body, generally indicated at 126, having a longitudinal axis A. The body 126 includes a plurality of fins 128 extending therealong and disposed in spaced angular relationship with respect to each other. In the embodiment illustrated herein, the body 126 includes four fins 128 spaced at 90° relative to one another. The fins 128 are adapted to engage the medullary canal in a removably stable fashion. However, those having ordinary skill in the art will appreciate that the body 126 of the intramedullary stem 118 may have any number of fins 128 disposed at any angle relative to each other and have any convenient shape. Alternatively, the body 126 may or may not employ fins of the type illustrated herein.

In one embodiment, the body 126 of the intramedullary stem 118 includes an intra-articular end 130 having base plate 132 disposed at the proximal end 134 of the body 126 and a distal end 136 disposed remote from the proximal end 134. The body 126 may also have a tapered cross-section disposed along the longitudinal axis A from the proximal end 134 to the distal end 136 of the body 126 of the intramedullary stem 118. In one embodiment, the fins 128 may have a 2° taper, gradually narrowing from the proximal end 134 to the distal end 136 of the stem. The distal end 136 may terminate in a bullet-like tip 140. However, those having ordinary skill in the art will appreciate that the exact shape of the distal end 136 can vary and that the taper may differ from approximately 2°. Moreover, the shape and size of the distal end 136 as well as the extent of the taper may be a function of the various sizes of the stems that may be employed with patients of different sizes. Those having ordinary skill in the art will appreciate from the description herein that the body 126 of the intramedullary stem 118, and its distal end 136, can have any shape that facilitates stability of the implant in the medullary canal and that further facilitates the insertion and removal of the device, and that assists in providing a press-fit of the stem in the medullary canal, so as to provide axial and rotational stability.

The inlet 120 is located in the base plate 132 of the body 126. Similarly, the plurality of cadets 122 are disposed between the outer surface 142 of at least one of the plurality of fins 128. In the embodiment illustrated herein, the outlets 122 are disposed along the longitudinal length of the body 126 of the intramedullary stem 118 in the valleys 144 defined between adjacent fins. The size and shape of the plurality of outlets 122 may vary depending on a number of factors including, but not limited to, the type of antibiotic fluid and other agents that pass through the stem 118, the desired pressure and flow of the fluid-borne antibiotic, as well as various patient factors, such as age. In addition and in one embodiment, the plurality of outlets 122 may vary in size, ranging from a smaller size at the proximal end of the stem, to a larger size at the distal tip, in order to compensate for a loss in pressure. In any event, those having ordinary skill in the art will appreciate that the size, location along the body 126 of the intramedullary stem 118, as well as the number of the outlets 122 may vary pursuant to a number of factors, all of which are within the scope of the present invention.

In the embodiment illustrated in FIGS. 3-5, the outer surface of the plurality of adjacent fins 128 is generally planer or smooth. However, another embodiment of the intramedullary system is, generally indicated at 218 in FIG, 6, where like numerals increased by 100 are used to designate like structure with respect to the stem illustrated in FIGS. 3-5. In this embodiment, the fins 228 may include longitudinally extending irregular outer surfaces 242 that are adapted to engage the medullary canal and that allow the flow of fluid-borne antibiotic between the fins 228 and the medullary canal. More specifically, in the embodiment illustrated here, the irregular surfaces 242 may define a plurality of serrations that present peaks 243 and valleys 245, whereby the peaks 243 are in contact with the medullary canal and the valleys 245 present openings through which fluid-borne antibiotic may pass. However, those having ordinary skill in the art will appreciate that the outer surface 142, 242 of the fins 128, 228 may take any geometric shape that is calculated to advance the dispersion fluid-borne antibiotic throughout the medullary canal.

Figure 6:
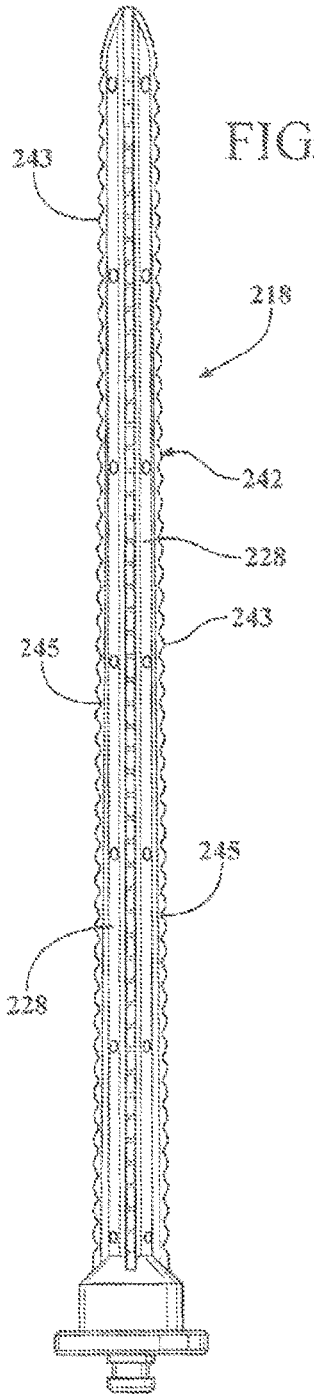
FIG. 6 is an elevational view of another embodiment of the intramedullary stem of the present invention.

As noted above, the intramedullary stem of the present invention forms a part of an antibiotic implant assembly 112. One such assembly is illustrated in FIGS. 7-12 and is particularly adapted for use in the first stage of a two-stage knee re-implantation process. To this end, the present invention may include a tibial intramedullary stem, generally indicated at 250. The tibial intramedullary stem 250 is adapted to be removably mounted within the medullary canal of a tibia bone. Similarly, the assembly of the present invention may also include a femoral intramedullary 350 stem that is adapted to be removably mounted within the medullary canal of the femoral bone. Like reference numerals increased by 100 with respect to the intramedullary stem 118 described in FIGS. 3-5, are used to describe like structure for the tibial intramedullary stem 250. Similarly, like reference numerals increased by 200 with respect to the intramedullary stem 118 described in FIGS. 3-5 are used to designate like structure with respect to the femoral intramedullary stem 350 illustrated in FIGS. 7-12. It should also be noted that the intramedullary stems 250, 350 employ the structure of the outer surface 242 of the fins 228 illustrated in FIG. 6.

Figure 8:
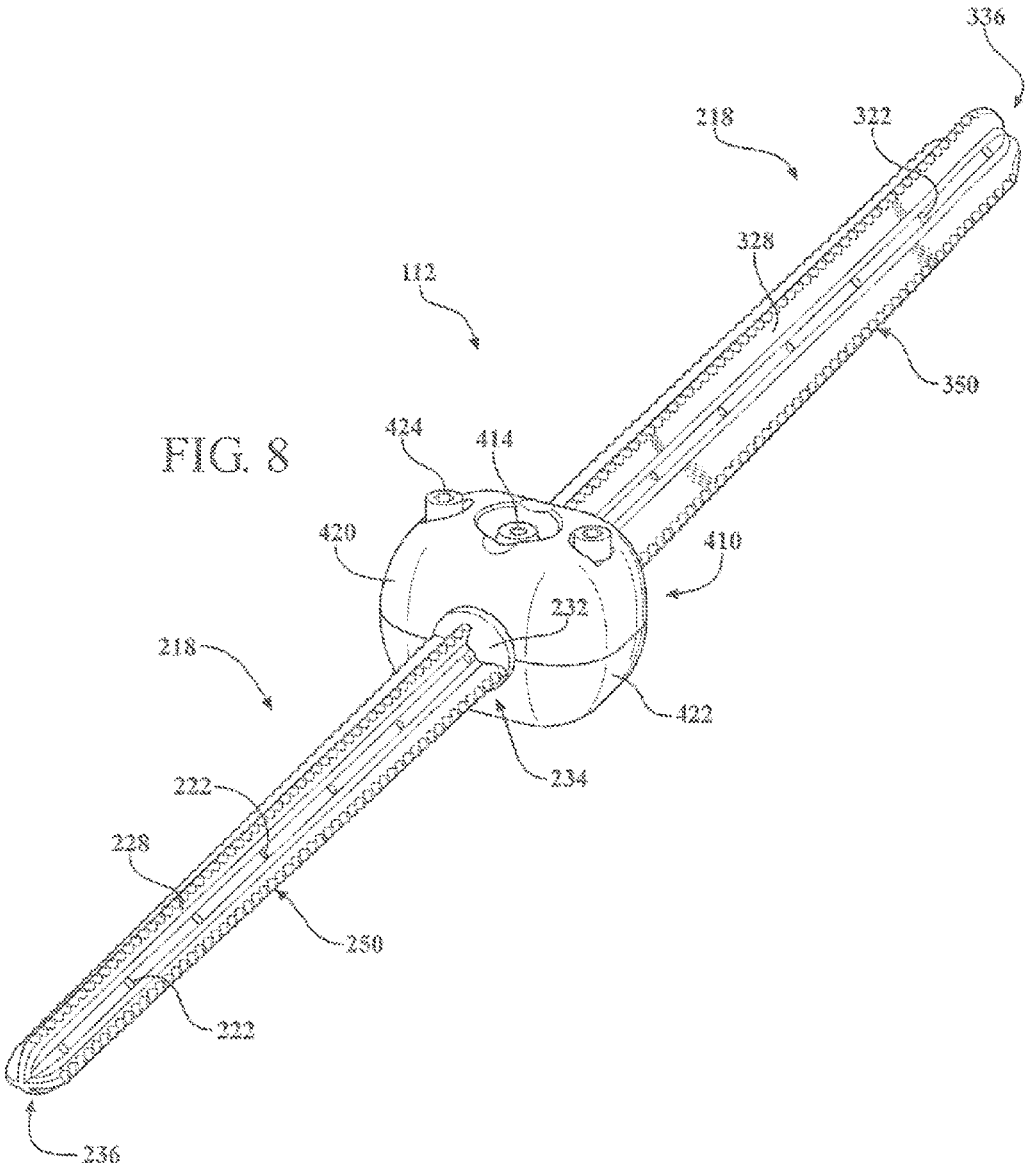
FIG. 8 is a perspective view of the implant assembly of the present invention.
Figure 9:
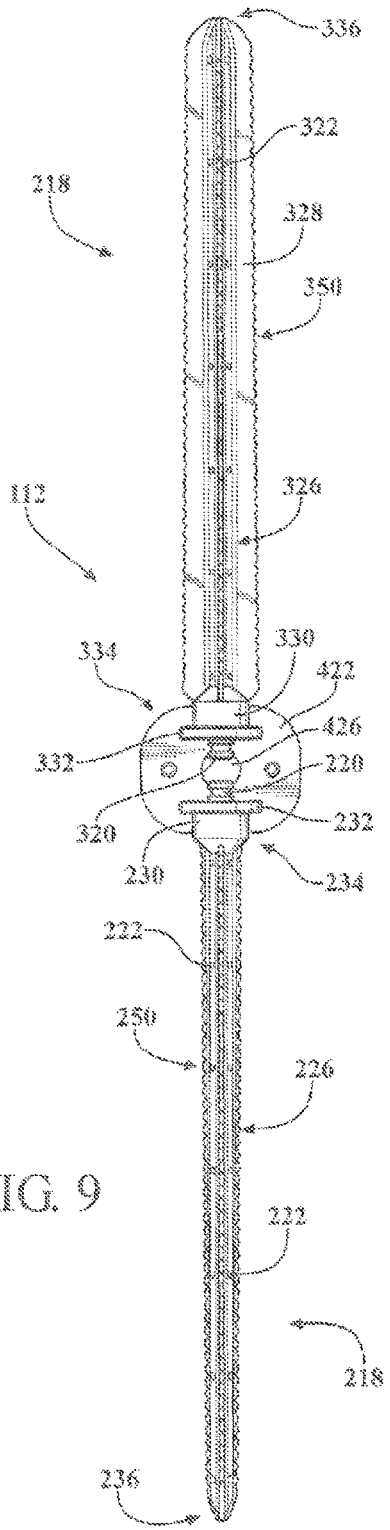
FIG. 9 is a top plan view of the implant assembly of the present invention showing the anterior half of the coupler removed.
Figure 10:
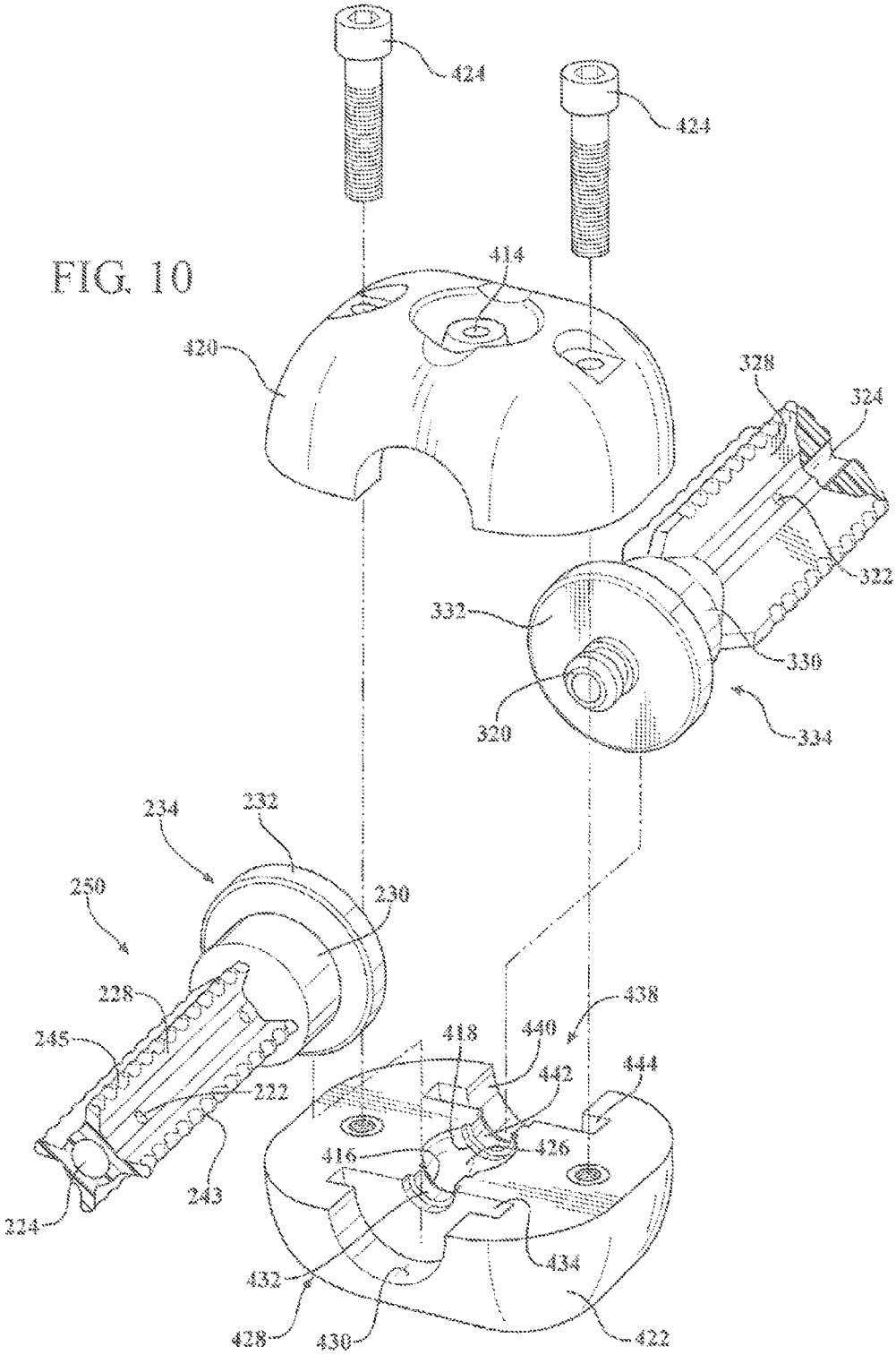
FIG. 10 is a partial enlarged exploded view of the coupler and tibial and femoral intramedullary stems.

Like the intramedullary stem illustrated in FIGS. 3-5, the tibial intramedullary stem 250 includes a body 226 with an intra-articular end 230 having a base plate 232 disposed at the proximal end 234 of the body and the distal end 236 disposed remote from the proximal end 234 (FIGS. 8-10). An inlet 220 (FIG. 9-11) is formed in the base plate 232 to the body 226 and a plurality of outlets 222 are disposed along the longitudinal length of the body 226. A channel 224 (FIG. 10) extends between the inlet 220 and the plurality of outlets 222 for purposes of distributing fluid-borne antibiotic and other fluid-borne agents into the medullary canal of a tibia bone. Similarly, like the intramedullary stem 118 illustrated in FIGS. 3-5, the femoral intramedullary stem 350 includes a body 326 with an intra-articular end 330 having a base plate 332 disposed at the proximal end 334 of the body 326 and the distal end 336 disposed remote from the proximal end 334. An inlet 320 is formed in the base plate 332 to the body 326 and a plurality of outlets 322 are disposed along the longitudinal length of the body 326. A channel 324 (FIG. 10) extends between the inlet 320 and the plurality of outlets 322 for purposes of distributing fluid-borne antibiotic and other fluids into the medullary canal of a femur bone. From the description herein taken along with the drawings, and with the exception of the irregular outer surface of the fins, those having ordinary skill in the art will appreciate that both the tibial and femoral intramedullary stems 250, 350 include all of the features and structural components as the intramedullary stem 118 illustrated in FIGS. 3-5 and described above.

As noted above and illustrated in FIG. 2, the implant assembly also includes a coupler, generally indicated at 410. The coupler 410 operatively interconnects the tibial intramedullary stem 250 and the femoral intramedullary stem 350 and acts to stabilize the joint defined therebetween. The system also includes a pump, generally indicated at 114. The pump 114 is disposed in fluid communication with the source of fluid-borne antibiotic 116 as well as other fluid-borne agents and the intramedullary stems 118, 250, 350 via the coupler 410. The pump 114 acts to control the delivery of titratable fluid-borne antibiotic from the source of fluid-borne antibiotic to the inlet 120, 220, 320 of the intramedullary stems 118, 250, 350 via a conduit 412 or any suitable tubing or other delivery means. In addition, the system may also include a source of cleansing/debriding fluid. In this case, the pump 114 further acts to control the delivery of cleansing fluid in intermittent pulsatile levage fashion to the inlet 120, 220, 320 of the intramedullary stems, as will be described in greater detail below. In addition, the pump 114 may also be employed to remove excessive fluid from the medullary canal and surrounding tissue prior to the reintroduction of fresh antibiotic, irrigating fluid, or other fluid-borne agents into the stem, the synovial joint, and the surrounding medullary canal to facilitate the cleaning of the treated tissue. From the preceding description, those having ordinary skill in the art will appreciate that the present invention facilitates the control of a the frequency, duration, dosage and pressure of the fluid-borne antibiotic and any other agents administered by the system in a sustainable and renewable manner. Thus, the present invention facilitates a far better sterile wound bed in a much shorter time than is achievable using the current standard of care.

Figure 7:
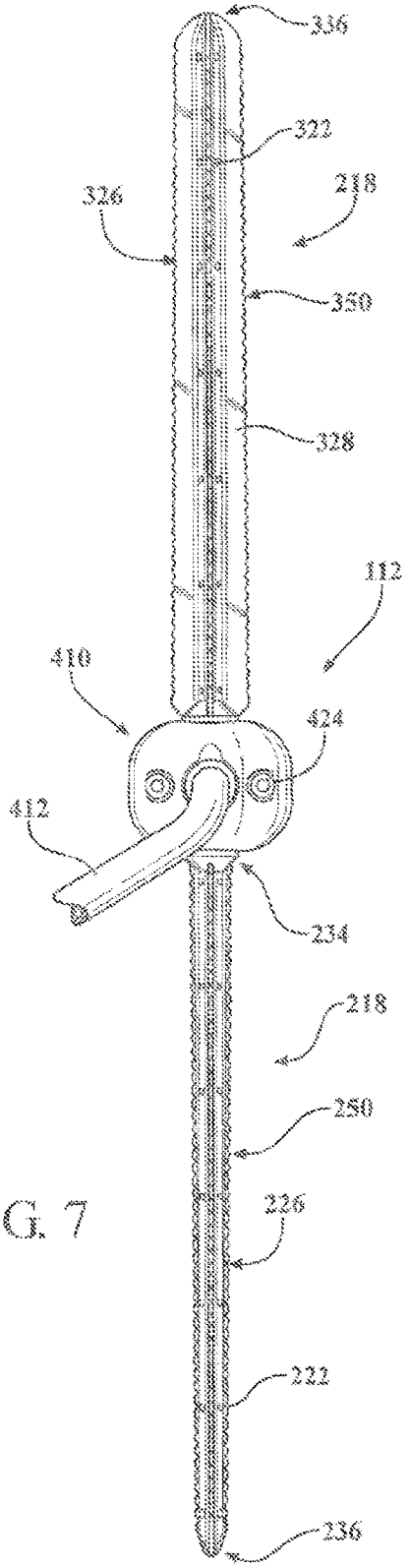
FIG. 7 is a top plan view of the implant assembly of the present invention.

As best shown in FIG. 10, the coupler 410 includes an inlet 414 that is adapted for fluid communication with the source of fluid-borne antibiotic 116 as well as at least one outlet 416, 418 in fluid communication with the inlets 220, 320 to the tibial 250 and femoral 350 intramedullary stems. The coupler 410 acts to distribute the fluid-borne antibiotic from the source of fluid-home antibiotic 116 to the plurality of outlets 222, 322 through the channels 224, 324 of the tibial and femoral intramedullary stems 230, 350. Likewise, those having ordinary skill in the art will appreciate that the coupler 410 also functions to distribute cleansing fluid and any other fluid-borne agents for any purpose directly into the synovial joint and into the medullary canal. In addition, as best shown in FIGS. 7, 8 and 12, the coupler 410 acts to hold the tibial and femoral intramedullary stems 250, 350 rigidly together in longitudinal alignment.

Figure 11:
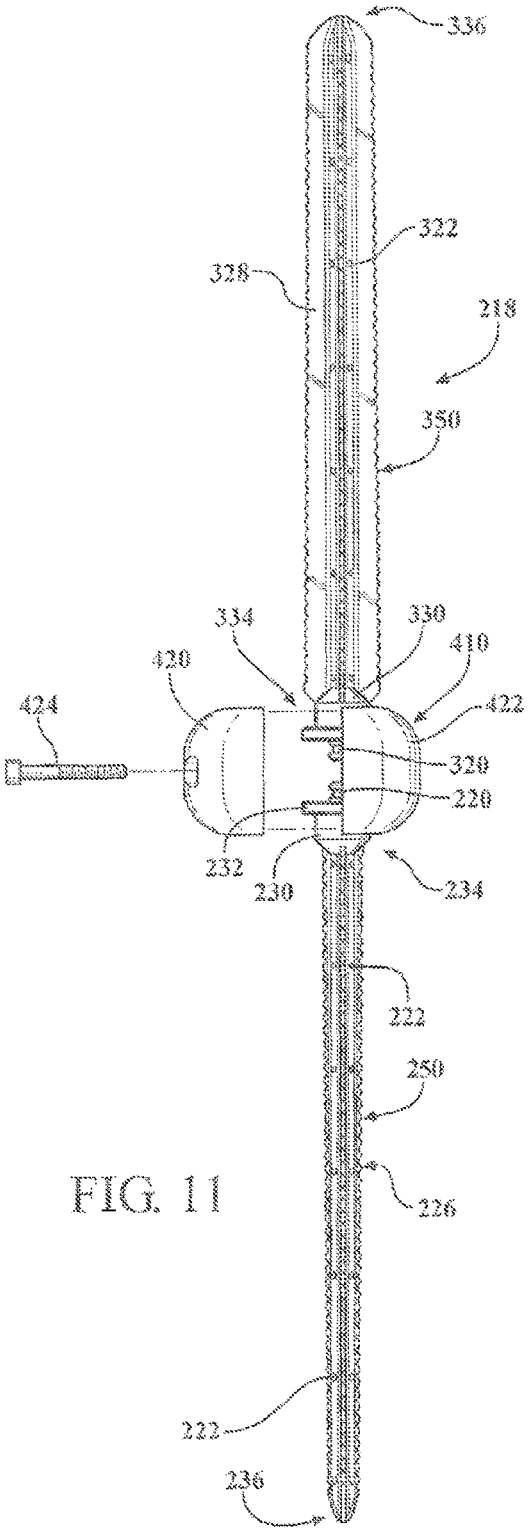
FIG. 11 is a side exploded view of the implant assembly of the present invention illustrating the assembly of the anterior half to the posterior half of the coupler.

More specifically and as best shown in FIGS. 9-11, the coupler 410 may be divided into anterior 420 and posterior 422 half sections that are operatively mounted together in sealed fashion using fasteners 424 of any suitable type. Together, the anterior 420 and posterior 422 halves of the coupler 410 define a reservoir 426 disposed in fluid communication with the inlet 414 to the coupler 410 as well as the inlets 220, 320 to the tibial and femoral intramedullary stems 250, 350. The coupler 410 includes a tibial stem receptacle, generally indicated at 428, that is adapted to receive the proximal end 234 of the body 226 of the tibial intramedullary stem 250 so as to establish fluid communication between the reservoir 426 and the inlet 220 to the intramedullary stem 250. Referring specifically to FIG. 10, the tibial stem receptacle 428 includes an inlet port 430, a nipple section 432, and a transverse portion 434 extending between the inlet port 430 and the nipple 432. The intra-articular end 234 of the intramedullary stem 250 is adapted to be snugly received in the inlet port 430. Similarly, the base plate 232 is adapted to be received in the transverse portion 434 and the inlet 220 is adapted to be received in the nipple portion 432 of the tibial stem receptacle 428. A gasket (not shown) may be employed at the inlet 220 to the intramedullary stem 250 to provide a proper seal between the inlet 220 of the stem 250 and the nipple portion 432 of the tibial stem receptacle 428.

Similarly, the coupler 410 includes a femoral stem receptacle, generally indicated at 438, adapted to receive the proximal end 334 of the body 326 of the femoral intramedullary stem 350 so as to establish fluid communication between the reservoir 426 and the inlet 320 to the femoral intramedullary stem 350. The femoral stem receptacle 438 includes an inlet port 440, a nipple section 442, and a transverse portion 444 extending between the inlet port 440 and the nipple section 442. The intra-articular end 334 of the femoral interamedullary stem 350 is adapted to be snugly received in the inlet port 440. Similarly, the base plate 332 is adapted to be received in the transverse portion 444 and the inlet 320 is adapted to be received in the nipple section 442 of the femoral stem receptacle 438. A gasket may also be employed at the inlet 320 to the femoral intramedullary stem 350 to establish an appropriate seal at this juncture with the nipple section 442 and the stem receptacle 438. Other seals may be employed to make the coupler fluid-tight as necessary. Thus, the stem receptacles 428, 438 in both ends of the coupler 410 are complimentarily shaped with respect to the intra-articular ends 234, 334 of the tibial and femoral intramedullary stems 250, 350 such that the stems are rigidly held in place by the coupler 410 when it is fully assembled, as illustrated, for example, in FIGS. 7, 8, 9 and 12.

As noted above, the tibial and femoral intramedullary stems 250, 350 may have a 2° taper gradually narrowing from the proximal to the distal end of the device. The tibial and femoral stems 250, 350 may have increasing lengths with each increase in stem diameter. Both the tibial and femoral stems 250, 350 may increase in diameter by 1 mm increments from approximately 14 mm to 22 mm at the base of the stems. This allows for a "press fit" in the intramedullary canal for axial and rotational stability. The intra-articular ends 234, 334 of the stems may all have one standard diameter and may be solid circumferentially for an axial length, such as 25 mm so that any proximal end of any stem will fit into any coupler. In any event, those having ordinary skill in the art will appreciate that the dimensions set forth herein are merely representative and are not meant to limit the size and shape of the components of the system.

Figure 14:
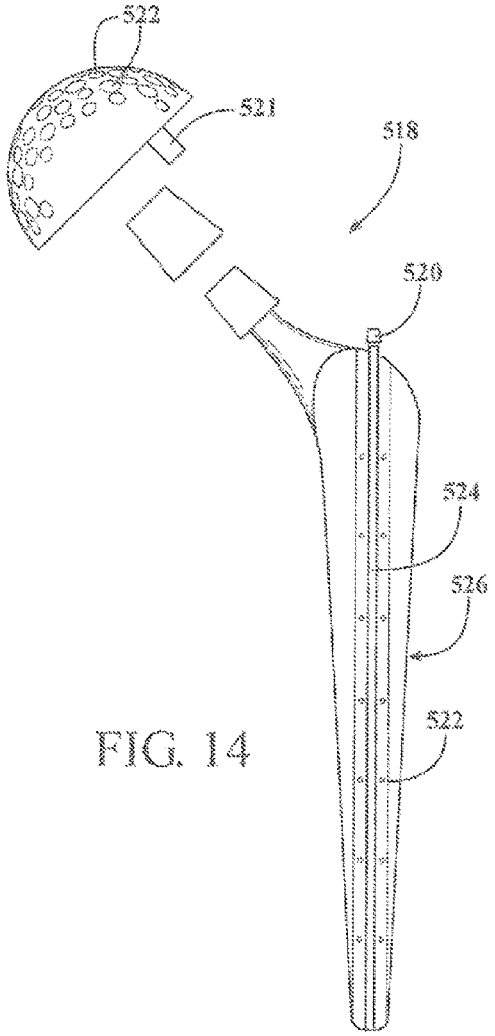
FIG. 14 is an exploded partial cross-sectional side view of the femoral intramedullary stem illustrated in FIG. 13.

Another embodiment of the antibiotic implant assembly of the present invention is illustrated in FIGS. 14-15. In this embodiment, the antibiotic delivery device is particularly adapted for use in stage one of a two-stage re-implantation process for a hip prosthesis. Like reference numerals increased by 400 with respect to the intramedullary stem 118 described in FIGS. 3-5, are used to designate like structure for the femoral intramedullary stem 518. Like the embodiment illustrated in FIGS. 3-12, the antibiotic delivery device includes a femoral intramedullary stem 518 that is adapted to be removably mounted into a medullary canal of a femur bone. In this case, the stem 518 is mounted at the upper portion of the femur bone. The femoral intramedullary stem 518 includes a body 526 having a proximate end 534 and a distal end 536 disposed remote from the proximate end 534. The stem 518 also includes a femoral head 560 and neck 562 extending from the proximal end 534 of the body 526 and between the body 526 and the femoral head 560. In one embodiment, the femoral head 560 and neck 562 are modular components. In its operative mode, the femoral neck 562 will be supplied in various incremental lengths, such as 5 mm increments, so that the space between the body 526 and the femoral head 560 may be customized for any given patient to maintain soft tissue tension of the hip in order to achieve stability and resistance to dislocation of the femoral head 560 and the socket. The femoral intramedullary stem 518 also includes at least one inlet 520, 521. However, in the embodiment illustrated herein, the body 526 includes more than one inlet, as will be described in greater detail below. In addition, the body 526 and the femoral head 560 have a plurality of outlets 522 and a channel 524 extending between the at least one inlet 520, 521 and the plurality of outlets 522 for delivering fluid-borne antibiotic from the inlet 520, 521 to the plurality of outlets 522 so as to distribute the antibiotic along the intramedullary canal as well as the socket of the hip joint in a controlled fashion. In this context, those having ordinary skill in the art will appreciate that the body 526 of the femoral intramedullary stem 518 illustrated in FIGS.

14-15 may have any of the other structure and features described with respect to the stems illustrated in FIGS. 3-12 above.

In the embodiment illustrated in FIGS. 14-15, the body 526 includes an inlet 520 and the femoral bead includes a separate inlet 521. Both inlets 520, 521 are in fluid communication with the source of fluid-borne antibiotic 116. The femoral head 560 has a hemispherical shape that is complimentarily received in the socket of the hip joint. In its operative mode, the femoral bead 560 will have a range of sizes in, for example, 1 mm increments, so that the head may be customized to fit a particular socket in any given patient. In this way, and as explained in greater detail below, the fluid-borne antibiotic is distributed directly through both the medullary canal of the femur bone as well as at the socket of the hip joint in a controlled fashion. Like the embodiment disclosed above, the flow of the antibiotic may be controlled by the pump 114. Similarly, the pump 114 may be used to disperse any type of fluid, such as cleansing fluid, in intermittent pulsatile levage fashion throughout the device.

In its operative mode, the antibiotic implant assembly, its individual intramedullary stems, as well as the entire system is employed in the first stage of what is an abbreviated two-stage re-implantation process. This process begins with the removal of the infected implants and aggressive debridement of the medullary canal. As noted above, in a traditional two-stage re-implantation, an antibiotic cement spacer would be placed between the tibia and femur bones in a knee as well as the upper portion of the femur and hip socket, in connection with a re-implantation of a hip. The wound would then be closed and would heal completely in the next six to twelve weeks before the patient would return for the second stage. This extended period of time between the first and second stages is necessary, in part, because the antibiotic is distributed fern the cement using elusion principles and is essentially uncontrolled.

However, in the abbreviated two-stage re-implantation employing the antibiotic delivery system of the present invention, the intramedullary stem 118, 218, 250, 350, 518 is mounted in the respective bone and provides direct antibiotic irrigation of the wound once the system is installed in both the tibia and femur (in the case of a knee replacement) or in the upper portion of the femur and hip socket (in the case of a hip replacement). Moreover, as best show in FIG. 12, the coupler 410 in combination with the tibial and femoral intramedullary stems 250, 350 acts to stabilize the joint and provides the necessary spacing between the tibia and femur bones. The wound may be covered with a polyurethane continuously connected porous sponge (for example, Granufoam manufactured by KCl). This porous sponge also occupies deep and superficial wound space. The incisional wound edges are then completely sewn over the negative pressure wound therapy sponge except for the area just large enough to allow a suction disk to be attached to the sponge. The open area of the incision is typically about 6 cm to 8 cm in length, however, those having ordinary skill in the art will appreciate that the incision can have any suitable length. The location of the incision is proximal incision on the knee, and distal incision on the hip. An occlusive see-through dressing is then applied. This is incorporated directly over the antibiotic in flow tubing and the outgoing wound suction tubing.

The direct infusion of antibiotic, such as Vancomycin, into the infected joint cavity allows for a very high level of drug concentration to be delivered in a fast and titratable fashion. This is in contrast to solely relying on the traditional antibiotic cement spacer to release the antibiotic through elusion principles alone, which is uncontrollable and typically starts out with most of the antibiotic released within the first few days, then gradually tapering off over the next weeks to months.

The present invention also takes advantage of concentration gradients. Over a typical 24-hour period, 4 g of Vancomycin could be delivered directly into the wound bed at the site of the infection at a concentration of approximately 13.3 mg per mm. In contrast, traditional IV antibiotic delivery systems, in which 1 g of antibiotic are given every 24 hours, will achieve a serum concentration level of around 10 μg to 20 μg per mm, and even less of a level in the actual joint space itself through diffusion. Those having ordinary skill in the art will appreciate that the practice among surgeons may vary and so different types of antibiotics in different concentrations may be preferred by different surgeons under different circumstances. Nevertheless, in the example set forth above, there is a concentration difference of a 1,000 fold or more in what concentration the actual joint space itself is projected to see between the two techniques. In addition, and using the traditional two-stage technique described in the background section of this application, there is no way to control the overall amount or rate of antibiotic elusion from the cement spacer.

The intramedullary stems 118, 218, 250, 350, 518 of the present invention may be manufactured of any suitable material. However, one suitable material of note includes a copper alloy. Copper has recently been recognized by the U.S. Environmental Protection Agency as the first solid surface material to be registered under the Federal Insecticide, Fungicide and Rodentcide Act. According to the EPA registration, certain copper alloys continuously reduce bacterial contamination achieving approximately 99.9% reduction within two hours of exposure. In addition, copper alloys can also kill greater than 99.9% of bacteria within two hours of exposure. Moreover, certain copper alloys deliver continuous and ongoing antibacterial action, even alter repeated wear and re-contamination. Those having ordinary skill in the art will appreciate that many different types of copper alloys may be suitable for this purpose. However, in order for the alloys to have antibacterial properties, it is believed that they must contain at least 65% copper. As presently best understood, there are currently 48 cast alloys which are included in the Group II Copper Alloys which have between 85% and 95% copper. In any event, those having ordinary skill in the art will appreciate that the present invention is not limited to any specific copper alloy or any particular material.

Like the stems, in one preferred embodiment the coupler 410 may also be metallic and may be manufactured using a copper alloy. Multiple couplers may be available, each having a variable thickness and transverse dimension that act to separate the abutting ends of the stems by, for example 5 mm increments, to allow the distance between the tibial and femoral stems to be customized in order to allow proper distraction of the joint cavity (for example between 25 mm and 40 mm), until the desired tension on the ligaments could be obtained. As noted above, in addition to the pump delivering the antibiotic fluid, the system 110 may also employ a negative pressure wound therapy to remove antibiotic irrigation fluid and to aid in the eradication of infection through principles unique to that technology.

The antibiotic delivery system 110 and the associated implant 112 assembly of the present invention overcomes the disadvantages in the related art in providing a modular, implantable device designed for short-term use of approximately one week as a part of an abbreviated two-stage re-implantation technique for treatment of a septic (infected) TJR of either the knee or the hip. The present invention provides structural rigidity to the joint and the limb during the period of time between the removal of an infected prosthesis and the re-insertion of a new prosthesis. This allows the patient to be mobile, while minimizing pain. In addition, the implant assembly 112 maintains joint space while acting as a temporary spacer. This maintains proper length of vital structures, including ligaments, muscles, tendons, neurovascular structures, etc., until the new prosthesis can be implanted. The system 110 and the individual components thereof act to deliver a controlled and titratable antibiotic dosed directly into the synovial joint cavity and medullary canals via an infusion system. In addition, the system and its components act to irrigate and cleanse the medullary canals through a novel concept utilizing intermittent pulsatile levage.

The present invention has been described in an illustrative manner. It is to be understood that the terminology that has been used is intended to be in the nature of words of description rather than of limitation. Many modifications and variations of the present invention are possible in light of the above teachings. Therefore, within the scope of the appended claims, the present invention may be practiced other than as specifically described. In addition, those having ordinary skill in the art will appreciate from the foregoing description, taken along with the drawings, that the term "system" as used in the claims may encompass individual components of the system, such as the intramedullary stems, the implant assembly for both a knee and hip, as well as the entire system, including the implant assembly, the pump, and the source of antibiotic fluid. Thus, the term "system" as it is used in the claims does not necessarily encompass all of the components of the system and, depending on the scope of the individual claims, may refer to merely a subcomponent of that system.

What is claimed is:

[1. An antibiotic delivery system comprising:

a femoral intramedullary stem adapted to be removably mounted into a medullary canal of a femur bone, said femoral intramedullary stem including a body having a proximate end and a distal end disposed remote from said proximate end, said body including a plurality of fins extending therealong and disposed in spaced angular relationship with respect to each other so as to define valleys that provide fluid flow spaces disposed between adjacent fins, said fins adapted to engage said medullary canal in a removably stable fashion, a femoral head and a neck extending from said proximal end of said body and between said body and said femoral head, said femoral intramedullary stem including at least one inlet, and a plurality of outlets disposed along said stem and between an outer surface of one of said plurality of adjacent fins in said valleys and in fluid communication with said fluid flow spaces and a channel extending between said inlet and said plurality of outlets, said femoral head having a plurality of outlets and a channel extending between said at least one inlet and said plurality of outlets for delivering fluid-borne antibiotics from said at least one inlet to said plurality of outlets so as to distribute said antibiotic along said intramedullary canal and the socket of a hip joint in a controlled fashion.]

[2. An antibiotic delivery system as set forth in claim 1, wherein said body includes an inlet and said femoral head includes an inlet, both inlets being in fluid communication with a source of fluid-borne antibiotic.]

[3. An antibiotic delivery system as set forth in claim 1, wherein said femoral head has a hemispherical shape so as to be complimentarily received in the socket of a hip joint.]

[4. A method of treating an infected joint during a two-stage re-implantation of an orthopedic implant, said method comprising the steps of: removing the infected implants mounted to the medullary canal of a bone; debriding the medullary canal; installing an intramedullary stem into the medullary canal where the stem includes an inlet, a plurality of outlets and a channel extending between the inlet and the plurality of outlets; said stem including a plurality of fins extending along a longitudinal axis of the stem and disposed in spaced angular relationship with respect to each other so as to define valleys that provide fluid flow spaces disposed between adjacent fins and a plurality of outlets disposed along said stem and between an outer surface of one of said plurality of adjacent fins in said valleys and in fluid communication with said fluid flow spaces providing a source of fluid-borne antibiotic to the inlet of the intramedullary stem so as to distribute the antibiotic into the medullary canal in a controlled fashion.]

[5. A method of treating an infected orthopedic implant as set forth in claim 4, wherein said step of installing an intramedullary stem includes installing a tibial intramedullary stem into the medullary canal of the tibia bone and installing a femoral intramedullary stein into the medullary canal of a femur bone.]

[6. A method of treating an infected orthopedic implant as set forth in claim 5, wherein the method further includes the step of positioning a coupler between the tibial intramedullary stem and the femoral intramedullary stem so as to provide axial stability between the tibial and femoral intramedullary stems.]

[7. A method of treating an infected orthopedic implant as set forth in claim 6, wherein the method further includes the step of establishing fluid communication between the coupler and the inlet of the tibial and femoral intramedullary stems and providing fluid communication between the coupler and a source of fluid-borne antibiotic so as to distribute the antibiotic through the tibial and femoral intramedullary stems and along the medullary canals in a controlled fashion.]

*8. A system for treating infected tissue, the system comprising:*

*an intramedullary stem adapted to be removably mounted into a medullary canal of a bone, wherein the intramedullary stem comprises a body with a longitudinal axis, a proximal end, a distal end, an outer body surface adapted to engage the inner wall of the bone, an inlet in fluid communication with a fluid, a plurality of outlets disposed longitudinally along the outer body surface, and a channel extending between the inlet and the plurality of outlets, the body including a plurality of fins extending therealong and disposed so as to define valleys that provide fluid flow spaces disposed between adjacent fins, wherein the fluid is delivered to the plurality of outlets so as to distribute the fluid along the medullary canal in a controlled fashion; and*

*a fluid removal element fluidly coupled with the intramedullary stem configured to remove fluid from the medullary canal.*

*9. The system of claim 8, wherein the fluid removal element comprises a negative pressure wound therapy system.*

*10. The system of claim 9, further comprising a pump, wherein the pump applies a vacuum for the negative pressure wound therapy system.*

*11. The system of claim 10, wherein the pump pumps the fluid in a pulsatile fashion.*

*12. The system of claim 8, further comprising a spacer element.*

*13. The system of claim 12, further comprising an additional stem coupled to the intramedullary stem via the spacer.*

*14. The system of claim 8, wherein the plurality of outlets are disposed at least partially circumferentially along the outer body surface.*

*15. The system of claim 8, wherein the plurality of fins extend along the longitudinal axis of the body.*

*16. The system of claim 8, wherein the plurality of fins are spaced at least partially circumferentially along the outer body surface so as to define one or more valleys between adjacent fins.*

*17. The system of claim 8, wherein the plurality of fins are spaced evenly circumferentially along the outer body surface.*

*18. The system of claim 8, wherein an outer surface of the plurality of fins is irregularly contoured so as to form fluid flow spaces therealong and to permit the fluid to flow past the fluid flow spaces.*

*19. The system of claim 18, wherein the irregularly contoured outer surface of the plurality of fins comprises serrations.*

*20. The system of claim 8, wherein the intramedullary stem further comprises a base plate at the proximal end thereof.*

*21. The system of claim 20, wherein the inlet is disposed on the base plate.*

*22. The system of claim 8, further comprising a pump, wherein the pump is in fluid communication with a source of the fluid and the inlet of the intramedullary stem, wherein the pump acts to control delivery of the fluid to the medullary canal through the plurality of outlets of the intramedullary stem.*

*23. The system of claim 22, wherein the pump pumps the fluid in a pulsatile fashion.*

*24. A method of treating an infected joint, said method comprising:*

*installing an intramedullary stem into a medullary canal of a bone, wherein said installing comprises engaging an outer stem surface of the intramedullary stem to the inner wall of the bone, the outer stem surface comprising a plurality of fins extending therealong and disposed so as to define valleys that provide fluid flow spaces disposed between adjacent fins when engaging with the inner wall of the bone;*

*irrigating the infected joint using a fluid that moves through the intramedullary stem; and*

*removing the fluid.*

*25. The method of claim 24, further comprising removing one or more implants from an infected medullary canal of a bone.*

*26. The method of claim 24, further comprising debriding the medullary canal.*

*27. The method of claim 24, wherein the fluid comprises an antibiotic.*

*28. The method of claim 24, wherein the fluid is removed using a negative pressure wound therapy system.*

*29. An intramedullary implant for treating an infected hip joint, said intramedullary implant comprising:*

*a stem adapted to be removably mounted into a medullary canal of a bone, the medullary canal defined by an inner wall of the bone, wherein the stem comprises a longitudinal axis, a proximal end, a distal end, an outer stem surface adapted to engage the inner wall of the bone, an inlet, a plurality of outlets disposed longitudinally along the outer stem surface, and a channel extending between the inlet and the plurality of outlets, the stem including a plurality of fins extending therealong and disposed so as to define valleys that provide fluid flow spaces disposed between adjacent fins;*

*a head that is coupled to a neck, wherein the neck is disposed at the proximal end of the intramedullary stem; and*

*a fluid removal element fluidly coupled with the intramedullary stem configured to remove fluid from the medullary canal.*

*30. The implant of claim 29, wherein the fluid removal element comprises a negative pressure wound therapy system.*

*31. The implant of claim 30, further comprising a pump, wherein the pump applies a vacuum for the negative pressure wound therapy system.*

*32. The implant of claim 31, wherein the pump pumps the fluid in a pulsatile fashion.*

*33. The implant of claim 29, wherein the head comprises an outer head surface that is configured to engage a socket of a joint.*

*34. The implant of claim 33, wherein the head comprises a plurality of outlets disposed along the outer head surface and in fluid communication with the inlet of the intramedullary stem.*

*35. The implant of claim 34, wherein the fluid is further delivered from a fluid source to the plurality of outlets disposed along the outer head surface so as to distribute the fluid along the socket of the joint in a controlled fashion.*

*36. The implant of claim 29, wherein the head is releasably attached to the intramedullary stem.*

*37. The implant of claim 29, wherein the fluid moves throughout the head.*

* * * * *